United States Patent [19]

Karrasch et al.

[11] Patent Number: 5,279,605
[45] Date of Patent: Jan. 18, 1994

[54] FRANGIBLE SPIKE CONNECTOR FOR A SOLUTION BAG

[75] Inventors: Frank Karrasch, Wadsworth; Walter Makaryk, Mount Prospect, both of Ill.

[73] Assignee: Baxter International Inc., Deerfield, Ill.

[21] Appl. No.: 642,172

[22] Filed: Jan. 17, 1991

Related U.S. Application Data

[63] Continuation of Ser. No. 346,859, May 3, 1989, abandoned.

[51] Int. Cl.$^5$ ............................................. A61M 5/00
[52] U.S. Cl. .................................. 604/403; 215/256; 604/411
[58] Field of Search ............... 604/403–416, 905; 220/265, 266, 276; 215/253, 256

[56] References Cited

U.S. PATENT DOCUMENTS

| | | |
|---|---|---|
| Re. 31,082 | 11/1982 | Winchell . |
| 3,523,530 | 8/1970 | Pagones ............................ 604/263 |
| 3,523,530 | 8/1970 | Pagones et al. ................... 604/263 |
| 4,007,740 | 2/1977 | Owen ................................. 604/192 |
| 4,091,811 | 5/1978 | Bates et al. ....................... 604/263 |
| 4,201,208 | 5/1980 | Cambio, Jr. ...................... 604/411 |
| 4,201,406 | 5/1980 | Dennehey et al. ............... 604/411 |
| 4,253,501 | 3/1981 | Ogle ............................. 604/407 X |
| 4,340,049 | 7/1982 | Munsch ............................. 251/342 |
| 4,402,420 | 9/1983 | Chernack .......................... 220/266 |
| 4,412,834 | 11/1983 | Kulin et al. .................. 137/625.41 |
| 4,415,393 | 11/1983 | Grimes ............................. 220/266 |
| 4,432,766 | 2/1984 | Bellotti et al. ................... 604/283 |
| 4,435,177 | 3/1984 | Kuhlemann et al. ............. 604/263 |
| 4,457,749 | 7/1984 | Bellotti et al. ..................... 604/29 |
| 4,473,369 | 9/1984 | Lueders et al. .................. 604/244 |
| 4,500,788 | 2/1985 | Kulin et al. .................... 250/455.1 |
| 4,583,971 | 4/1986 | Bocquet et al. .................... 604/82 |
| 4,624,667 | 11/1986 | Rutnarak ........................... 604/414 |
| 4,657,535 | 4/1987 | Nishimura et al. .............. 604/263 |
| 4,911,696 | 3/1990 | Miyasaka et al. ................ 604/244 |
| 5,045,067 | 9/1991 | Ohnaka et al. ................... 604/244 |
| 5,053,003 | 10/1991 | Dadson et al. ..................... 604/28 |

FOREIGN PATENT DOCUMENTS

| | | |
|---|---|---|
| 71.3102 | 10/1972 | France . |
| WO88/06902 | 5/1988 | Japan . |
| 1399868 | 9/1975 | United Kingdom . |

*Primary Examiner*—Robert A. Hafer
*Assistant Examiner*—Sam Rimell
*Attorney, Agent, or Firm*—Charles R. Mattenson; Allan O. Maki; Paul C. Flattery

[57] ABSTRACT

A one-piece unitary frangible spike connector for insertion into solution containers includes a spike body formed with a closure on one end thereof and a tubing receptacle on the other end thereof. An internal conduit extends from the tubing receptacle through the spike body partially into the closure. The frangible spike connector is broken apart along a reduced diameter portion tapered or formed at an angle to form a spike connected to the conduit on the spike body when the closure is broken off the spike body.

11 Claims, 2 Drawing Sheets

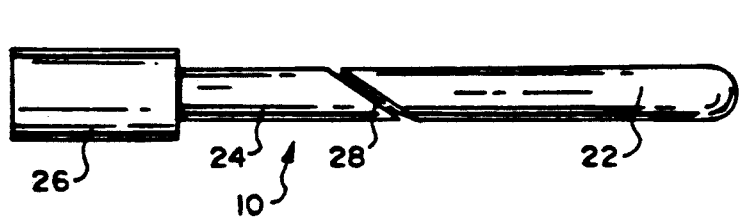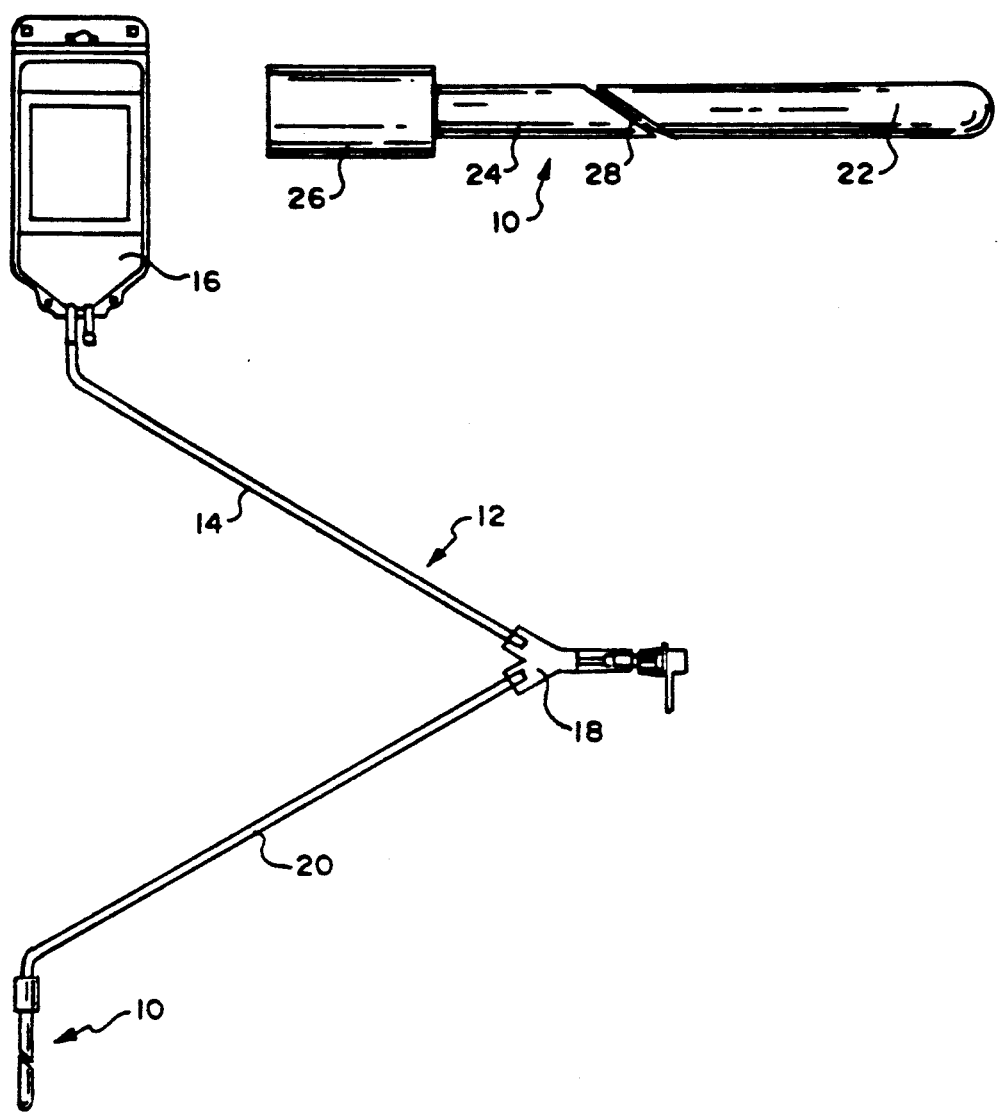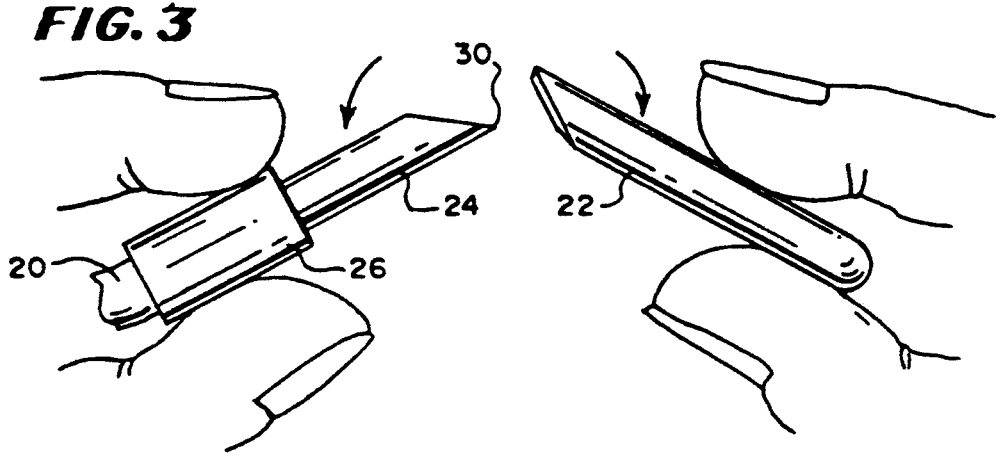

FRANGIBLE SPIKE CONNECTOR FOR A SOLUTION BAG

This is a continuation of copending application Ser. No. 07/346,859, filed on May 3, 1989, now abandoned.

BACKGROUND OF THE INVENTION

The present invention concerns a spike connector of the type utilized to connect a tubing set to a medical solution container or bag. More particularly, the present invention is directed to a unitary molded one-piece frangible spike connector.

Many medical solution containers typically have an outlet port extending therefrom, with the port having a transverse diaphragm adapted for breakage by a spike from a tubing set. When the spike is inserted into the port, the transverse diaphragm is broken and the medical liquid can flow from the medical container through the spike and the tubing set to the patient.

In certain applications a sterile medical solution is utilized and it is important that the sterility of the system be maintained. For example, in peritoneal dialysis a dialysate solution is introduced into a patient's peritoneal cavity and is thereafter drained from the peritoneal cavity to the original solution container or elsewhere.

The medical procedure known as continuous ambulatory peritoneal dialysis (CAPD), described in U.S. Pat. No. 4,239,041, has rapidly grown in clinical acceptance as the technique of choice for maintaining many patients who have lost kidney function. Peritoneal dialysis solution is inserted in the peritoneal cavity, whereby diffusion exchange takes place between the solution and the bloodstream across the peritoneal membrane, to remove by diffusion the waste products which are normally excreted through the kidneys, typically solutes such as sodium and chlorine ions and the other materials normally excreted by the body such as urea, creatinine and water.

In the CAPD technique, the patient is surgically equipped with an implanted catheter which communicates between the peritoneal cavity and the exterior. Peritoneal dialysis solution is passed into the peritoneal cavity where dialysis of urea and the like takes place between the solution and the blood passing through blood vessels in the peritoneum, which is the lining of the peritoneal cavity. Thereafter, this peritoneal dialysis solution is removed from the peritoneal cavity, carrying with it diffused breakdown products from the blood. Fresh dialysis solution is then passed into the peritoneal cavity, and this process of filling and emptying is repeated several times.

In the CAPD technique, as with all techniques of peritoneal dialysis, peritonitis is one of the most significant risks. Peritonitis can result if connections are made between the peritoneal catheter and a set communicating with a source of dialysis solution in a manner which permits even a very small number of microorganisms to enter the catheter and to be flushed into the peritoneal cavity.

Examples of other areas where sterile connections are desirably made, and in which the present invention may be utilized can include the processing of blood and its fractions, the mixing of sterile solutions, connecting Foley catheters with urinary drainage bags, and hemodialysis or blood oxygenation procedures especially with patients who have diminished immunological capability. Also, the invention may be used to provide sterile conditions to a protective enclosure surrounding an indwelling catheter or the like.

Many types of spike connectors and connector assemblies have been proposed for use with such solution containers. Various types of sterilization also have been suggested, alone or in conjunction with various spike connectors. Typically, the spike connector assemblies are multipiece units which have a molded body with a metal needle inserted therein and a cover member inserted thereover. Molded spike connectors also have been utilized with sterilization techniques and/or with separate covers for the spike connector assemblies. Each of these prior assemblies require numerous pieces and multiple assemby steps.

It would be desirable to have a unitary one-piece spike connector, which also includes an integral cover for the spike connector and can be formed in a single step.

SUMMARY OF THE INVENTION

In accordance with the present invention, a frangible spike connector is provided having an integral closure therewith. The spike conduit of the frangible spike connector cannot be internally contaminated prior to use since the internal conduit of the spike is covered by the closure.

The frangible spike connector includes a spike body with a tubing receptacle in one end and the closure on the opposite end closing the conduit. When the frangible spike connector is mounted on the tubing or tubing set, the closure prevents contamination into the spike conduit and prevents the spike from inadvertently being utilized or accidentally causing a puncture wound. The body includes a tapered or beveled edge therearound along which the body fractures when broken to provide the spike. The tubing receptacle and spike closure can take many forms and can include wings or flat portions for ease in fracturing the frangible spike connector. Preferably, the frangible spike connector is a one-piece molded assembly, from which the closure can be broken off to expose the spike and conduit for insertion into the solution container.

BRIEF DESCRIPTION OF THE DRAWINGS

FIG. 1 is a view of a first frangible spike connector embodiment of the present invention on a tubing set coupled to the port of a medical solution container;

FIG. 2 is an enlarged plan view of the frangible spike connector of FIG. 1;

FIG. 3 is a perspective view of the frangible spike connector of FIG. 1, being broken apart;

DESCRIPTION OF THE PREFERRED EMBODIMENTS

Figure 4:
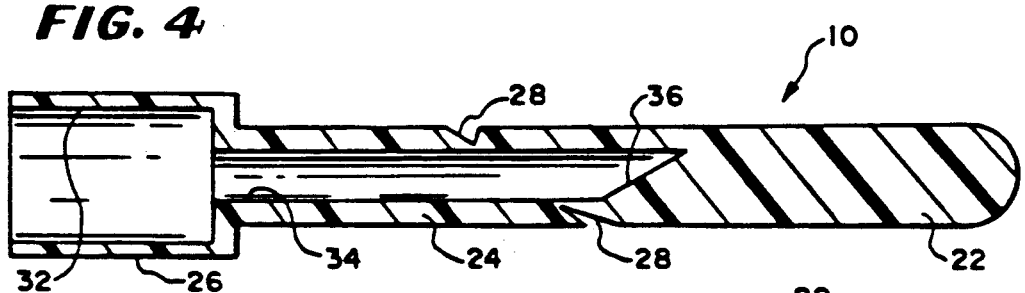
FIG. 4 is an enlarged cross-sectional view of the frangible spike connector of FIG. 1.

Referring to FIG. 1, a first embodiment of the frangible spike connector of the present invention is designated generally by the reference numeral 10. The frangible spike connector is connected to a tubing set 12, which includes, for example purposes only, a first tubing segment 14, which is connected at one end to a conventional medical solution container or bag 16. The other end of the tubing segment 14 is connected to a conventional Y connector 18. A second tubing segment 20 is also connected at one end to the Y connector 18 and at the other end to the frangible spike connector 10.

One example of a utilization of the tubing set 12, is in the CAPD technique. The Y connector 18 preferably is a luer connector and is coupled to the patient (not illustrated) and the fluid from the bag 16 is introduced into the patient. The frangible spike connector 10 can be fractured when it is desired to utilize the segment 20 to drain the fluid from the patient where a sterile outer spike surface is not needed. The spike then can be inserted into a second drain container or bag (not illustrated). Until the frangible spike connector 10 is fractured, no contamination can occur inside the frangible spike connector 10, which is sealed by the tubing segment 20 on one end and a closure 22 on the other end, as best illustrated in FIGS. 2-5.

Referring to FIG. 2, the frangible spike connector 10 is formed, such as by conventional injection molding, having a spike body 24 on one end and the closure 22 on the other end. The spike body 24 includes a tubing receptacle 26 into which the tubing 20 is sealingly inserted in a conventional manner. The closure 22 is connected to the spike body 24 by a beveled reduced thickness portion 28.

Referring to FIG. 3, when it is desired to utilize the frangible spike connector 10, a user grasps the receptacle 26 with one hand and the closure 22 with the other hand and breaks the two apart along the bevel portion 28 forming a spike 30. The closure 22 is discarded and the spike 30 is inserted into a container port (not illustrated). The portion 28 also can be tapered to form a tapered spike, if so desired.

Figure 5:
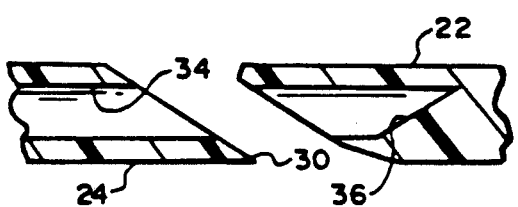
FIG. 5 is a partial cross-sectional view of the frangible spike connector of FIG. 4, broken apart.

The structure of the one-piece molded frangible spike connector 10 is best illustrated in FIGS. 4 and 5. The tubing receptacle 26 includes an internal conduit 32, sized to accommodate the tubing 20 therein. The conduit 32 communicates with a conduit or passageway 34 formed in the spike body 24 and ending in a closed end 36 in the closure 22. Thus, the conduits 32 and 34 are sealed from outside exposure when mounted on the tubing 20, until the frangible spike connector 10 is broken apart as illustrated in FIG. 5.

Figure 6:
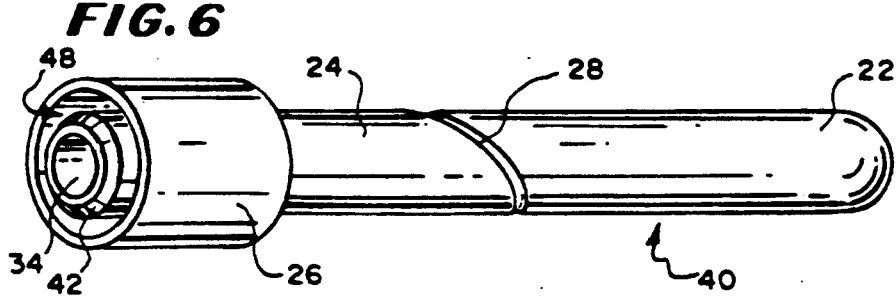
FIG. 6 is a perspective view of a second embodiment of the frangible spike connector of the present invention.
Figure 7:
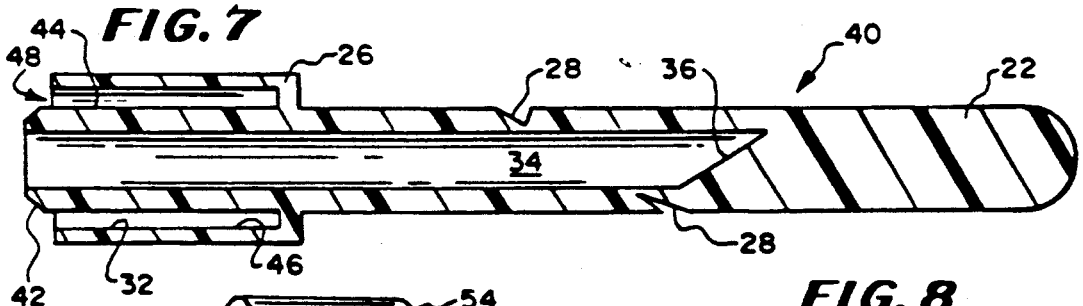
FIG. 7 is an enlarged cross-sectional view of the frangible spike connector of FIG. 6.

A second embodiment of the frangible spike connector of the invention is designated generally by the reference numeral 40 in FIGS. 6 and 7. The same reference numerals are utilized for the portions of the frangible spike connector 40 which are unchanged from those of the frangible spike connector 10. The frangible spike connector 40 has an extended tubular portion 42 forming a tubing mandrel which extends the passageway 34 into the conduit 32. An outer wall 44 of the tubular portion 42 is spaced from an inner wall 46 of the conduit 32 and forms an annular recess 48, into which the tubing 20 can be inserted over the mandrel 42.

Figure 8:
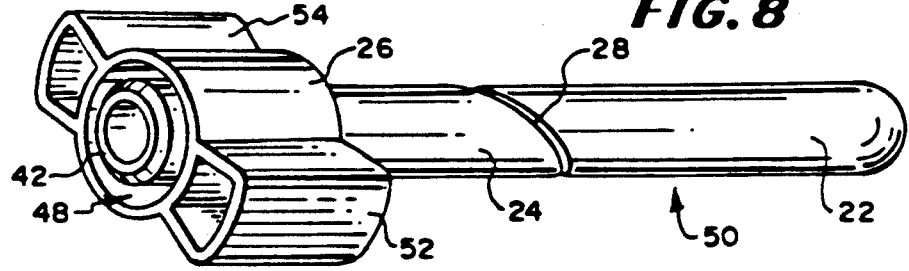
FIG. 8 is a perspective view of a third embodiment of the frangible spike connector of the present invention.

A third embodiment of the frangible spike connector of the invention is designated generally by the reference numeral 50 in FIG. 8. The frangible spike connector 50 is substantially the same as the frangible spike connector 40, with the addition of a pair of tabs or wings 52, 54. The tabs 52, 54 can be grasped by the user to insert the spike 30 into the drainage container and also to aid in orienting the frangible spike connector 50 to break the closure 22 from the spike body 24 to form the spike 30.

Figure 9:
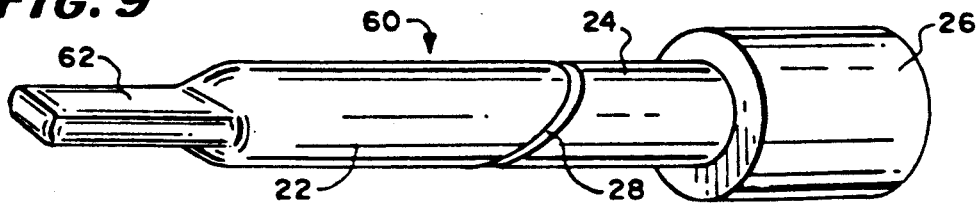
FIG. 9 is a perspective view of a further embodiment of the frangible spike connector of the present invention.

A further embodiment of the frangible spike connector of the invention is designated generally by the reference numeral 60 in FIG. 9. The frangible spike connector 60 includes a flat tip 62 molded thereto to aid the user in orienting the frangible spike connector 60 to break the closure 22 from the spike body 24.

One primary use of the frangible spike connectors 10, 40, 50 and 60 is in a CAPD set 12, illustrated in FIG. 1. The set 12 will at least include the tubing segments 14 and 20, a luer type Y connector and cover therefor and the frangible spike connectors 10, 40, 50 and 60 and the tubing segment 14 will be connected to either a cap (not illustrated) or a container such as the container 16. The frangible spike connectors 10, 40, 50 and 60 generally are intended for drainage or other uses wherein the outer surface can be non-sterile, however, the frangible spike connectors 10, 40, 50 and 60 could also be sterilized on the outside for other uses.

Many modifications and variations of the present invention are possible in light of the above teachings. The dimensions of the frangible spike connectors 10, 40, 50 and 60 are not critical. The angle and depth of the bevel portion 28 are not critical and can be replaced by a conical reduction in thickness if desired. The frangible spike connectors 10, 40, 50 and 60 can be formed from any suitable, preferably moldable, material which has sufficient mechanical properties and is non-toxic to the fluids utilized therewith. Generally, the moldable material will be a plastic or plastic like material. One actual frangible spike connector 40 is formed from molded polycarbonate material having a wall thickness of the portion 28 of 0.013 inches formed at an angle of 45° to the axis of the frangible spike connector 40. The diameter of the closure 22 is 0.200 inches, the outer receptacle 26 is 0.380 inches and the length of the frangible spike connector 40 is 1.973 inches. The material and the thickness of the reduced diameter portion 28 controls the force necessary to be utilized by the user to break the closure 22 from the spike body 24. It is, therefore, to be understood that within the scope of the appended claims, the invention may be practiced otherwise than as specifically described.

What is claimed and desired to be secured by Letters Patent of the United States is:

1. An end closure member for a length of tube that can be transformed by the user into an angle-tipped spike connector, the member comprising
   a molded one piece body having a longitudinal axis and a portion having a uniform circular exterior diameter, the molded body enclosing an interior passageway aligned along the longitudinal axis and having a tubing receptacle at one end communicating with the interior passageway, the molded body also having a closure wall at its other end closing the interior passageway, and
   a continuous line of reduced thickness on the molded body located entirely in said portion between its tubing receptacle end and its closure wall end, the line extending at a nonperpendicular angle relative to the longitudinal axis for creating a score line along which the closure wall can be selectively separated by the user from the remainder of the body to create an open angle-tipped spike end that communicates with the interior passageway and that has the same exterior diameter as said portion of the molded body.

2. The end closure member defined in claim 1 and wherein the reduced thickness area forms an elliptical bevel around the body.

3. The end closure member defined in claim 1 and including a tubing mandrel formed in the tubing receptacle end in communication with the interior passageway.

4. The end closure member defined in claim 1 and wherein the tubing receptacle end includes a pair of orientation wings extending outwardly therefrom.

5. The end closure member defined in claim 1 and wherein the closure wall end includes a flat tip orientation portion extending therefrom.

6. A tubing set for use in performing continuous ambulatory peritoneal dialysis in which the tubing set is coupled to a patient's tube communicating with the patients's peritoneal cavity and also connected to solution that is conveyed into and drained from the peritoneal cavity using the tubing set, the tubing set comprising
    a first tubing segment connected to one leg of a Y-type connector that can be coupled to the patient's tube for draining solution from the patient's peritoneal cavity,
    a second tubing segment connected at one end to the other leg of the Y-type connector for conducting fluid into the patient's peritoneal cavity, and
    a molded one piece body attached to the other end of the second tubing segment, the body having a longitudinal axis and an exterior diameter, the molded body enclosing an interior passageway aligned along the longitudinal axis and having a tubing receptacle at one end communicating with the interior passageway and attached to the second tubing segment, the molded body also having a closure wall at its other end closing the interior passageway and the attached second tubing segment, and a continuous line of reduced thickness on the molded body between its tubing receptacle end and its closure wall end, the line extending at a nonperpendicular angle relative to the longitudinal axis for creating a score line along which the closure wall can be selectively separated by the user from the remainder of the body to create an open angle-tipped spike end that communicates with the interior passageway and that has the same exterior diameter as the molded body.

7. A tubing set defined in claim 6 and wherein the reduced thickness area forms an elliptical bevel around the body.

8. A tubing set defined in claim 6 and including a tubing mandrel formed in the tubing receptacle end in communication with the interior passageway.

9. A tubing set defined in claim 6 and wherein the tubing receptacle end includes a pair of orientation wings extending outwardly therefrom.

10. A tubing set defined in claim 6 and wherein the closure wall end includes a flat tip orientation portion extending therefrom.

11. A method of molding an end closure member for a length of tube that can be transformed by the user into an angle-tipped spike connector, the method comprising the steps of
    molding an elongated one piece body having a longitudinal axis and an exterior diameter and enclosing an interior passageway aligned along the longitudinal axis,
    forming on the body a closure wall closing the interior passageway, and
    forming on the body, in a portion having an otherwise uniform circular exterior diameter, a continuous line of reduced thickness entirely within said portion and extending at a nonperpendicular angle relative to the longitudinal axis for creating a score line along which the closure wall can be selectively separated by the user from the remainder of the body to create an open angle-tipped spike end that communicates with the interior passageway and that has the same exterior diameter as the molded body.

* * * * *